United States Patent [19]

Rosenbaum et al.

[11] Patent Number: 5,447,538
[45] Date of Patent: Sep. 5, 1995

[54] COMPOSITION FOR DYEING HAIR COMPRISING IN ADMIXTURE A NON-EXHAUSTED VEGETABLE POWDER, A DIRECT DYE AND A SOLID DILUENT

[75] Inventors: Georges Rosenbaum, Asnieres; Jean Cotteret, Franconville; Jean-Francois Grollier, Paris, all of France

[73] Assignee: L'Oreal, Paris, France

[21] Appl. No.: 951,195

[22] Filed: Sep. 28, 1992

Related U.S. Application Data

[63] Continuation-in-part of Ser. No. 782,128, Oct. 25, 1991, abandoned, which is a continuation of Ser. No. 50,423, May 18, 1987, abandoned, which is a continuation of Ser. No. 541,685, Oct. 13, 1983, abandoned, which is a continuation of Ser. No. 352,103, Feb. 25, 1982, abandoned.

[30] Foreign Application Priority Data

Feb. 27, 1981 [FR] France .............. 81 03946

[51] Int. Cl.$^6$ ............. A61K 7/13; C09B 6/00
[52] U.S. Cl. ............ 8/405; 8/426; 8/428; 8/435; 424/74
[58] Field of Search ........ 8/405, 426, 428, 435; 424/74

[56] References Cited

U.S. PATENT DOCUMENTS

| | | | |
|---|---|---|---|
| 406,071 | 6/1889 | Vogt | 8/405 |
| 924,359 | 6/1909 | Kearney et al. | 424/74 |
| 4,190,064 | 2/1980 | Gordon et al. | 424/70 |
| 4,358,286 | 11/1982 | Grollier et al. | 8/425 |
| 4,460,488 | 7/1984 | Grollier | 252/89.1 |

FOREIGN PATENT DOCUMENTS

| | | |
|---|---|---|
| 74078 | 12/1917 | Australia . |
| 1127790 | 12/1956 | France . |
| 1559594 | 3/1969 | France . |
| 2030581 | 10/1969 | France . |
| 2030581 | 11/1970 | France . |
| 344906 | 12/1921 | Germany . |
| 0648226 | 10/1977 | U.S.S.R. . |
| 0648226 | 2/1979 | U.S.S.R. . |

OTHER PUBLICATIONS

Keller: "Mysterious Herbs & Roots", p. 311, 1978.
Wall; Mecial Times and Long Island Medical Journal; "Cosmetics", Nov. 1933.

*Primary Examiner*—Ceila Chang
*Attorney, Agent, or Firm*—Cushman Darby & Cushman

[57] ABSTRACT

A cosmetic composition in the form of a powder for dyeing hair when diluted comprising a mixture of (1) particles of a vegetable substance of the non-exhausted type and not naturally containing dye principles wherein at least 95 percent by weight of the particles of said vegetable substance have a granulometry lower than 180 microns, (2) at least one direct dye and (3) at least one solid diluent, the said solid diluent being such that it exhibits in a 40% aqueous solution or dispersion a viscosity lower than or equal to 150 centipoises at ambient temperature.

4 Claims, No Drawings

COMPOSITION FOR DYEING HAIR COMPRISING IN ADMIXTURE A NON-EXHAUSTED VEGETABLE POWDER, A DIRECT DYE AND A SOLID DILUENT

This is a continuation-in-part of application Ser. No. 07/782,128, filed Oct. 25, 1991 now abandoned which is a continuation of application Ser. No. 07/050,423, filed May 18, 1987, now abandoned, which is a continuation of application Ser. No. 06/541,685, filed Oct. 13, 1983, now abandoned, which is a continuation of Ser. No. 06/352,103, filed Feb. 25, 1982, now abandoned.

The present invention relates to a powdered composition for dyeing hair, the powdered composition being diluted with water or milk prior to its application to the hair.

More particularly the present invention provides a stable composition capable of providing after dilution a dye preparation known as a "cataplasm dye" having an unctuous consistency and being easy to apply to the entire head of hair.

Since the advent of synthetic dyes, the dyeing of hair has become a quite common operation and it is generally effected with the aid of aqueous dye preparations which are employed as such or are diluted at the time of use with developer agents which are usually oxidizing agents.

These aqueous dye preparations can be provided in various forms and more particularly in the form of creams, liquids or gels, having a more or less thick consistency and having a variable solvent or water content.

The hair dye substances used in these preparations are, at the present, generally dyes of synthetic origin which permits, by using them either alone or in admixture, to impart to the hair a wide variety of particularly desirable shades.

These hair dyes can be either oxidation dye, that is to say, substances whose dyeing power is developed only by the presence of an oxidizing agent or direct dyes which are capable of coloring the hair by themselves without the addition of any developer agent.

Mention must also be made, when referring to these hair coloring substances of dyes termed "natural dyes" and principally those of vegetable origin.

This case of dyes which includes not only plant powders or extracts but also the isolated molecules or compounds responsible for the dyeing power, provide the non-negligible advantage of generally being inoffensive which is not always the case with the use of certain synthetic dyes which have been found responsible for various allergies.

A representative dye of vegetable origin which has been widely employed for a significant number of years and is still in favor in numerous countries, is henna powder which has a yellowish green color and is obtained from leaves of henna (*Lawsonia inermis*).

The active principle of henna is lawsone, (2-hydroxy-1,4-naphthoquinone), present in the leaves of henna in the form of a glucoside.

However, natural dyes of vegetable origin, and more particularly henna, exhibit various disadvantages, a principal one of which is its poor storage stability in aqueous containing vehicles or carriers.

It is possible, however, to use the powder of henna leaves as such, that is to say, without a pre-mixed aqueous carrier by diluting the same at the time of use with the aid of warm water so as to form a paste-like product that is then applied to the hair. However, in this case, certain other disadvantages are encountered during the preparation of the paste-like product and in the application of the same to the hair. Thus, it is not always possible to obtain excellent or acceptable impregnation of the hair due to the poor consistency of the composition which is produced from a coarsely ground powder.

Moreover, it is very difficult to expect perfect reproducibility of a color obtained using such a product since the amount of active principle (lawsone in the case of henna) can vary significantly from one lot to another depending on the origin of the plant and its time of harvest.

In addition to this disadvantage the pH conditions are not always optimum for dyeing. Further, it is often difficult to subsequently effect on hair so dyed a permanent wave which exhibits a good hold, which can be attributed to the presence in the dye mass of too large an amount of hair sheathing agents.

It has now been found that these various disadvantages associated with the use of dyes of natural origin, and in particular dyes of vegetable origin, can be avoided by mixing them with various components which are capable of imparting to the composition an unctuous consistency, thus facilitating their application to the entirety of the hair. This result is obtained according to the present invention by combining the natural direct dyes with a non-exhausted vegetable substance of the non-exhausted type and not naturally containing dye principles having a determined granulometry and with a solid diluent.

This non-exhausted vegetable substance, while imparting to the composition good unctuousness after dilution, facilitates its removal and imparts both softness and a shiny appearance to the hair.

The use of the solid diluent compensates for variations caused by fluctuations between the physical characteristics of several lots of the same substance of natural origin, principally, the thickening power without modifying the dye concentration which is the sole guaranty of good dyeing power reproducibility.

The present invention thus relates to a cosmetic composition, provided in the form of a powder for dyeing hair when diluted, comprising in admixture:

(1) at least one non-exhausted vegetable powder wherein at least 95 percent by weight of the particles of said powder have a diameter or granulometry lower than 180 microns and preferably lower than 125 microns and more particularly lower than 80 microns,
(2) at least one direct dye of natural origin, and
(3) at least one solid diluent, said diluent being such that it exhibits in a 40% aqueous solution or dispersion, a viscosity, at ambient temperature, lower than or equal to 150 centipoises.

More particularly, the present invention relates to a milk or water dilutable composition in dry form for application in diluted form to human hair to color said hair comprising a mixture of (a) between 3 and 95 weight percent based on the total weight of said composition of a vegetable substance wherein at least 95 percent by weight of said particles have a granulometry below 180 microns, said vegetable substance being of the non-exhausted type and not naturally containing dye principles, said substance being selected from the group consisting of (1) the entire plant of wheat, (2)

the leaves of a plant selected from the group consisting of *cassis obovata*, chestnut tree and rosemary, (3) corn stalks and (4) the fruit of horsechestnut tree, (b) a direct dye in an amount of 0.05 to 30 percent by weight based on the total weight of said composition, said direct dye being selected from the group consisting of lawsone, hematoxylin, purpurin, alizarin, indigo and curcumin, and (c) a solid diluent present in an amount of 5 to 75 percent by weight based on the total weight of said composition, said solid diluent exhibiting in a 40% solution or dispersion in water, a viscosity, at ambient temperature, not greater than 150 centipoises, said solid diluent being selected from the group consisting of powdered milk, glucose, levulose, lactose, sorbitol, maltose, sucrose, starch, sodium carbonate and sodium citrate.

The composition according to the present invention, defined above, is particularly storage stable.

The non-exhausted vegetable substance in powder form is present in the composition of the present invention in an amount between 3 and 95 percent by weight, and preferably between 5 and 85 percent by weight, based on the total weight of the composition. This powder can be obtained by grinding and subsequent sieving the above defined vegetable substance.

This non-exhausted vegetable powder also does not naturally contain active dye principles. Thus, the powder can be from, for example, the entire plants of wheat, the leaves of a plant selected from the group consisting of *cassia obovata*, chestnut tree and rosemary; corn stalks; and the fruit of horsechestnut tree.

The direct dyes, isolated in the pure state or obtained synthetically, which are used in the composition of the present invention include, in particular:

lawsone-2-hydroxy-1,4-naphthoquinone,
hematoxylin-7,11b-dihydrobenz[b]indeno[1,2-d]pyran 3,4 6a, 9, 10 (6H)-pentol;
purpurin-1,2,4-trihydroxy anthraquinone or C.I. Natural Red 8;
alizarin-1,2-dihydroxy anthraquinone or C.I. Mordant Red 11;
indigo-[$\Delta^{2,2'}$-biindoline]-3,3'-dione; and
curcumin-1,7-bis[4-hydroxy-3-methoxy phenyl]-1,6-heptadiene-3,5-dione.

The solid diluent of the composition according to the present invention is generally present in an amount between 5 and 75 percent by weight based on the total weight of the composition.

This solid diluent exhibits in a 40% solution or dispersion of the same in water, a viscosity at ambient temperature, not greater than 150 centipoises.

The solid diluent is preferably powdered milk, glucose, levulose, lactose, sorbitol, maltose, sucrose, starch, sodium carbonate and sodium citrate.

In addition to the three main components of the composition according to the present invention, there can also be included therein synthetic dyes of non-natural origin in an amount ranging from 0.05 to 15 percent by weight based on the total weight of the powdered composition and principally those selected from nitrobenzene dyes, anthraquinone dyes, indoamine dyes, azo dyes or triphenylmethane dyes.

Moreover, the compositions according to the present invention can also contain conventional adjuvants such as alkalizing or acidifying agents including alkaline carbonates or solid organic acids; thickening agent such as cellulose derivatives, gums, pectins, alginates or carragenates; hair treating or conditioning agents; softening agents; bactericides; and perfumes.

At the time of use, the composition of the present invention is mixed with milk or water, preferably lukewarm, containing optionally a solvent such as a lower alcohol or glycol, in a weight ratio of milk or water/powder between 1–10/1 and preferably between 1–5/1.

The viscosity of the composition thus obtained can vary between 3 and 45 poises but preferably between 5 and 35 poises at ambient temperature. The pH of the composition obtained, depending upon the presence of an alkalizing or an acidifying agent, can range between 2.5 and 12, and preferably between 3 and 10.5.

The present invention also relates to a process for dyeing hair comprising diluting the above defined composition in milk or water wherein the ratio of said milk or water to the composition ranges from 1–10:1, applying the resulting diluted composition to the hair in an amount effective to dye the hair, permitting said diluted composition to remain in contact with the hair for a period of time ranging from 3 minutes to 2 hours and rinsing the hair with water.

This rinsing operation can, optionally, be followed by a shampoo in order to obtain better removal of any residual hair dye composition.

Because of the excellent unctuousness of the dye composition of the present invention there is obtained by this process good distribution thereof on the hair and consequently a uniform coloration.

The following non-limiting examples illustrate the present invention.

| Examples | 1 | 2 | 3 | 4 | 5 | 6 |
| --- | --- | --- | --- | --- | --- | --- |
| Lawson | 2 g | — | — | — | — | — |
| Hematoxylin | — | 2 g | — | — | — | — |
| Purpurin | — | — | 2 g | — | — | — |
| Alizarin | — | — | — | 2 g | — | — |
| Indigo | — | — | — | — | 2 g | — |
| Curcumin | — | — | — | — | — | 2 g |
| Powder of chestnut tree leaves | 50 g | — | — | — | — | — |
| Powder of corn stalks | — | 50 g | — | — | — | — |
| Powder of horse chestnut tree fruits | — | — | 50 g | — | — | — |
| Powder of wheat | — | — | — | 50 g | — | — |
| Powder of *cassia obovata* leaves | — | — | — | — | 50 g | — |
| Powder of rosemary leaves | — | — | — | — | — | 50 g |
| Red pectin 3G, sold by Unipectine | 3 g | 3 g | 3 g | 3 g | 3 g | 3 g |
| Anhydrous sodium carbonate | 5 g | 5 g | 5 g | 5 g | 5 g | 5 g |
| Powdered trioxymethylene | 0.3 g | 0.3 g | 0.3 g | 0.3 g | 0.3 g | 0.3 g |
| Lactose q.s.p. | 100 g | 100 g | 100 g | 100 g | 100 g | 100 g |

At the moment of use 10 g of the above powders are mixed with 20 g of water at 40° C. The resulting unctuous mixtures are applied on gray hair having 90% of white hair for 30 minutes at room temperature. After rinsing the hair and drying, the treated hair is shiny and exhibits the following shades:

Example 1: coppery golden shade
Example 2: iridescent violet shade
Example 3: auburn shade
Example 4: violet shade
Example 5: ash grey shade
Example 6: yellow golden shade.

What is claimed is:

1. A milk or water-dilutable composition in dry form for application in diluted form to human hair to color said hair consisting essentially of a mixture of:
   (a) between 3 and 95 weight percent based on the total weight of said composition of particles of a vegetable substance wherein at least 95 percent by weight of said particles have a granulometry below 180 microns, said vegetable substance being of the non-exhausted type and not naturally containing dye principles, said substance being selected from the group consisting of (1) the entire plant of wheat, (2) the leaves of a plant selected from the group consisting of *cassia obovata*, and (3) corn stalks,
   (b) a direct dye in an amount of 0.05 to 30 percent by weight based on the total weight of said composition, said direct dye being selected from the group consisting of lawsone, hematoxylin, purpurin, alizarin, indigo and curcumin, and
   (c) a solid diluent present in an amount of 5 to 75 percent by weight based on the total weight of said composition, said solid diluent exhibiting in a 40% solution or dispersion in water a viscosity, at ambient temperature, not greater than 150 centipoises, said diluent being selected from the group consisting of powdered milk, glucose, levulose, lactose, sorbitol, maltose, sucrose, starch, sodium carbonate, and sodium citrate.

2. A process for dyeing hair comprising diluting the composition of claim 1 in milk or water wherein the ratio of said milk or water to said composition ranges from 1–10:1, applying the resulting diluted composition to the hair in an amount effective to dye the hair, permitting said diluted composition to remain in contact with the hair for a period of time ranging from 3 minutes to 2 hours and rinsing the hair with water.

3. A milk or water-dilutable composition in dry form for application in diluted form to human hair to color said hair consisting essentially of a mixture of:
   (a) between 3 and 95 weight percent based on the total weight of said composition of particles of a vegetable substance wherein at least 95 percent by weight of said particles have a granulometry below 180 microns, said vegetable substance being of the non-exhausted type and not naturally containing dye principles, said substance being selected from the group consisting of (1) the entire plant of wheat and (2) corn stalks,
   (b) a direct dye in an amount of 0.05 to 30 percent by weight based on the total weight of said composition, said direct dye being selected from the group consisting of lawsone, hematoxylin, purpurin, alizarin, indigo and curcumin, and
   (c) a solid diluent present in an amount of 5 to 75 percent by weight based on the total weight of said composition, said solid diluent exhibiting in a 40% solution or dispersion in water a viscosity, at ambient temperature, not greater than 150 centipoises, said diluent being selected from the group consisting of powdered milk, glucose, levulose, lactose, sorbitol, maltose, sucrose, starch, sodium carbonate, and sodium citrate.

4. A process for dyeing hair comprising diluting the composition of claim 3 in milk or water wherein the ratio of said milk or water to said composition ranges from 1–10:1, applying the resulting diluted composition to the hair in an amount effective to dye the hair, permitting said diluted composition to remain in contact with the hair for a period of time ranging from 3 minutes to 2 hours and rinsing the hair with water.

* * * * *